(12) United States Patent
Matter et al.

(10) Patent No.: US 12,378,367 B2
(45) Date of Patent: Aug. 5, 2025

(54) AQUEOUS THICKENING COMPOSITION

(71) Applicant: COATEX, Genay (FR)

(72) Inventors: Yves Matter, Reyrieux (FR); Denis Ruhlmann, Genay (FR); Jean-Marc Suau, Lucenay (FR)

(73) Assignee: COATEX, Genay (FR)

( * ) Notice: Subject to any disclaimer, the term of this patent is extended or adjusted under 35 U.S.C. 154(b) by 0 days.

(21) Appl. No.: 17/626,673

(22) PCT Filed: Jul. 8, 2020

(86) PCT No.: PCT/FR2020/000201
§ 371 (c)(1),
(2) Date: Jan. 12, 2022

(87) PCT Pub. No.: WO2021/014054
PCT Pub. Date: Jan. 28, 2021

(65) Prior Publication Data
US 2022/0259384 A1   Aug. 18, 2022

(30) Foreign Application Priority Data
Jul. 19, 2019 (FR) .................................. 1908247

(51) Int. Cl.
| C08J 3/05 | (2006.01) |
| A61K 8/06 | (2006.01) |
| C08K 5/103 | (2006.01) |
| C09D 7/44 | (2018.01) |

(52) U.S. Cl.
CPC ............... *C08J 3/05* (2013.01); *A61K 8/062* (2013.01); *C08K 5/103* (2013.01); *C09D 7/44* (2018.01); *A61K 2800/48* (2013.01); *C08J 2367/00* (2013.01); *C08J 2371/02* (2013.01); *C08J 2375/02* (2013.01); *C08J 2375/08* (2013.01)

(58) Field of Classification Search
CPC ...... C08J 3/05; C08J 2367/00; C08J 2371/02; C08J 2375/02; C08J 2375/08; C09D 7/44; A61K 8/062; A61K 2800/48; C08K 5/103
See application file for complete search history.

(56) References Cited

U.S. PATENT DOCUMENTS

| 5,876,702 | A | * | 3/1999 | Gers-Barlag | .......... | C09K 15/30 |
| | | | | | | 514/939 |
| 6,433,056 | B1 | | 8/2002 | Burdick et al. | | |
| 6,479,573 | B2 | | 11/2002 | Burdick et al. | | |
| 2002/0052441 | A1 | | 5/2002 | Burdick et al. | | |
| 2018/0071198 | A1 | | 3/2018 | Lin et al. | | |
| 2022/0259384 | A1 | * | 8/2022 | Matter | ............... | C08G 18/2825 |

FOREIGN PATENT DOCUMENTS

| EP | 2630176 A2 * | 8/2013 | ............. A61K 8/062 |
| EP | 2 630 176 B1 | 7/2015 | |

OTHER PUBLICATIONS

International Search Report mailed on Nov. 4, 2020 in PCT/FR2020/000201 filed on Jul. 8, 2020, (2 pages).
Care Chemicals Division, "Lutensol® AT Types", Feb. 3, 2014, XP055675963, pp. 1-8.
Office Action issued Oct. 14, 2024, in corresponding Chinese Patent Application No. 202080049834.5, 6 pages.

* cited by examiner

Primary Examiner — Jiangtian Xu
(74) Attorney, Agent, or Firm — Oblon, McClelland, Maier & Neustadt, L.L.P.

(57) ABSTRACT

The invention pertains to the field of aqueous thickening compositions, particularly for increasing the viscosity of an aqueous paint or varnish composition, a detergent composition or a cosmetic composition, in particular a cosmetic composition comprising ethoxylated surfactant compounds. The composition according to the invention comprises at least 40% by weight of water and combines a particular thickening compound and a nonionic compound comprising at least one hydrophilic saccharide group attached to at least one linear or branched hydrophobic chain.

16 Claims, No Drawings

AQUEOUS THICKENING COMPOSITION

CROSS REFERENCE TO RELATED APPLICATIONS

This application is a national stage entry under 35 USC 371 of PCT/FR2020/000201, filed on Jul. 8, 2020, and claims priority to French Patent Application No. 19 08247, filed on Jul. 19, 2019. The entire disclosures of these related applications are incorporated herein by reference.

The invention relates to the field of aqueous thickening compositions, in particular compositions that make it possible to increase the viscosity of aqueous paint or varnish compositions, detergent compositions or cosmetic compositions, in particular a cosmetic composition comprising ethoxylated surfactant compounds. The composition according to the invention comprises at least 40% by weight of water and combines a particular thickening compound and a non-ionic compound comprising at least one hydrophilic osidic group bound to at least one straight or branched hydrophobic chain.

Numerous thickening agents are known to increase the viscosity of aqueous compositions, in particular polyurethane thickening agents. However, these thickening agents generally have a high viscosity in aqueous solution. Certain thickening agents in the prior art are in the form of a wax at room temperature. A high viscosity in aqueous solution makes them difficult to convey or handle, particularly when they are dispersed in the composition to be thickened. In particular, these thickening agents must have a viscosity that enables them to be pumped. Too high a viscosity can also cause problems when preparing these thickening agents.

To control this viscosity, thickening agents in the prior art are often diluted, in particular with water or with organic solvents. Also to control their viscosity, thickening agents in the prior art can be combined with plasticizer compounds, for example cyclodextrin, cyclodextrin derivatives or surfactant compounds, in particular ethoxylated surfactant compounds, anionic surfactant compounds or ethoxylated anionic surfactant compounds, as well as mixtures thereof.

These various means of controlling the viscosity of the thickening agents in the prior art have many drawbacks.

Diluting with water decreases the relative quantity of the thickening agent. The efficacy of the viscosity control is thus reduced. The use of organic solvents to dilute the thickening agent leads to the same problems, as well as to environmental problems and to the diffusion of volatile organic compounds.

Controlling the viscosity of the thickening agents in the prior art with plasticizer compounds also gives rise to problems. These problems can occur when using these thickening agents or when preparing them.

For example, the use of cyclodextrin, cyclodextrin derivatives, or surfactant compounds introduces ionic charges into the thickening agent. The presence of these ionic charges then makes the thickening agent sensitive to pH variations when it is used. This sensitivity then unpredictably disrupts the thickening efficacy.

Combining these plasticizer compounds with the thickening agents in the prior art leads to a relative decrease in the amount of thickening agent, which disrupts the viscosity control. The combined addition of water leads to the same problems due to its potential absorption by the surfactant compounds. Some surfactant plasticizer compounds can also disrupt or inhibit the thickening efficacy of the thickening agents in the prior art. If several methods of controlling the viscosity of the thickening agents in the prior art are combined, other problems may arise, in particular due to the chemical, physical or functional incompatibility between them. Combining different thickening agents can also lead to antagonistic effects.

Document CA 2816039 relates to a method of preparing polyurethanes that requires the presence of a metal carboxylic acid salt. Document U.S. Pat. No. 6,479,573 relates to a method for thickening an aqueous system using water-soluble polyurethanes or hydrophobic-terminated poly(acetal-polyethers).

There is therefore a need for improved thickening agents. These thickening agents must make it possible to control the different components of the viscosity of the aqueous compositions in which these agents are used. For example, for coating compositions, the thickening agents must make it possible to control the Brookfield viscosity at different shear gradients, the ICI viscosity as well as the Stormer viscosity.

Preferably, the thickening agents should also be partially or completely of natural origin. The stability of the thickening agents must also be improved, in particular: their stability during their preparation, during their transport or during their storage. Thickening agents must also retain their properties in spite of pH variations.

The composition according to the invention makes it possible to obtain solutions to all or part of the problems of the thickening agents in the prior art.

Thus, the invention provides an aqueous composition comprising at least 40% by weight of water, and
- at least one polyalkoxylated compound (a) chosen among a polyurethane compound (a1), a polyurethane-polyurea compound (a2), a polyether compound (a3), a polyester compound (a4), a polyurea compound (a5) and combinations thereof;
- at least one non-ionic compound (b) comprising at least one hydrophilic osidic group bound to at least one straight or branched hydrophobic chain.

The invention also provides an aqueous composition consisting of at least 40% by weight of water, at least one polyalkoxylated compound (a) and at least one non-ionic compound (b) comprising at least one hydrophilic osidic group bound to at least one straight or branched hydrophobic chain.

According to the invention, the composition according to the invention as well as compounds (a) and (b) are insensitive to pH variations, in particular to pH variations ranging from pH 2 to pH 12. Thus, compounds (a) and (b) do not cause any substantial change in the rheological properties of the composition according to the invention subject to pH variations, in particular pH variations ranging from pH 2 to pH 12, preferably pH variations ranging from pH 5 to pH 9. In particular, the viscosity of the composition according to the invention is unchanged or is changed by a value such that this change is not significant when this composition is used.

According to the invention, the quantities of compound (a) and of compound (b) can vary, in particular depending on the nature of these compounds or depending on the use of the composition according to the invention. Preferably, the dry/dry weight ratio (a/b) of the quantities of compound (a) and of compound (b) ranges from 0.1 to 10, preferably from 1 to 7.

The aqueous composition according to the invention comprises at least one compound (a). Preferably, compound (a) is a rheology-modifying compound, particularly a thickening compound. Also preferably, compound (a) is a non-ionic compound, more preferably an alkoxylated non-ionic compound. Also preferably, compound (a) is an associative compound, also more preferably an alkoxylated associative compound. Much more preferably, compound (a) is a non-ionic associative compound, even more preferably an alkoxylated non-ionic associative compound.

Preferably according to the invention, compound (a) is an associative compound. An associative compound (a) makes it possible to produce associative bonds when using the composition according to the invention. These associative bonds generally develop between chemical groups of the same nature, particularly between hydrophobic groups.

More preferentially, the polyalkoxylated compound (a) comprises at least one alkoxylated $C_2$-$C_4$ group, in particular at least one ethoxylated group or one propoxylated group. Preferably, the polyalkoxylated compound (a) comprises ethoxylated groups alone or in combination with propoxylated groups. Also preferably, compound (a) comprises from 10 to 2,000 alkoxylated $C_2$-$C_4$ groups, in particular from 100 to 1,500 ethoxylated or propoxylated groups. More preferably, the alkoxylated compound (a) comprises from 100 to 1,500 ethoxylated groups. Even more preferably, the alkoxylated compound (a) comprises from 250 to 1,500 ethoxylated groups.

Essentially according to the invention, the composition according to the invention comprises at least one compound (a) chosen among a polyurethane compound (a1), a polyurethane-polyurea compound (a2), a polyether compound (a3), a polyester compound (a4), a polyurea compound (a5) and combinations thereof.

Advantageously according to the invention, the composition according to the invention comprises at least one compound (a) chosen among a polyurethane compound (a1), a polyether compound (a3), a polyester compound (a4) and combinations thereof, particularly a combination of a polyurethane compound (a1) and of a polyether compound (a3) or a combination of a polyurethane compound (a1) and of a polyester compound (a4).

Preferably according to the invention, the polyurethane compound (a1) is a polyurethane compound (a1-1) prepared by reaction:
  of at least one isocyanate compound (A) independently chosen among a diisocyanate compound (A1), a polyisocyanate compound (A2) and combinations thereof;
  of at least one polyhydroxyl compound (B), preferably chosen among:
  a compound (B1) of formula (chem I):

wherein L independently represents a poly(alkylene glycol) residue and n independently represents a number ranging from 40 to 400;
  a compound (B1) of formula (chem I) combined with a non-alkoxylated compound (B2) comprising at least three hydroxyl groups;
  a polyalkoxylated compound (B3) comprising at least three hydroxyl groups;
  a compound (B4) of formula (chem II):

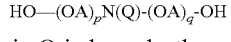

wherein Q independently represents a straight or branched $C_8$-$C_{32}$-alkyl group, OA independently represents an ethoxylated (—$CH_2CH_2O$—) group or a combination of ethoxylated (—$CH_2CH_2O$—) groups and of propoxylated (—$CH_2C(CH_3)O$—) groups and p and q independently represent a number ranging from 50 to 200;
  combinations thereof; and
  of at least one compound (C) chosen among a monoisocyanate compound (C1), a monohydroxyl compound (C2) and combinations thereof.

According to the invention, the diisocyanate compound (A1) comprises two isocyanate groups.

Preferably according to the invention, the polyisocyanate compound (A2) comprises more than 2 isocyanate groups or more than 2.2 isocyanate groups or more than 2.5 isocyanate groups. More preferably according to the invention, the polyisocyanate compound (A2) comprises more than 2.6 isocyanate groups or more than 2.7 isocyanate groups or more than 3 isocyanate groups. Also preferably according to the invention, the polyisocyanate compound (A2) comprises from 2.2 to 6 isocyanate groups, from 2.2 to 4 isocyanate groups, from 2.2 to 3.5 isocyanate groups, from 2.5 to 6 isocyanate groups, from 2.2 to 5 isocyanate groups, from 2.5 to 4 isocyanate groups, from 2.5 to 3.5 isocyanate groups, in particular from 2.6 to 3.3 isocyanate groups.

Preferably according to the invention, compound (B1) is a compound of formula (chem I) wherein:
  L independently represents a poly(ethylene glycol) residue; or
  n independently represents a number ranging from 50 to 400, preferably from 100 to 300; or
  L independently represents a poly(ethylene glycol) residue and n independently represents a number ranging from 50 to 400, preferably from 100 to 300.

More preferably according to the invention, compounds (B), (B1), (B3) and (B4) independently have a molar mass (Mw) measured by CES ranging from 1,500 to 20,000 g/mol, preferably from 2,000 to 20,000 g/mol, more preferentially from 4,000 to 15,000 g/mol.

Also preferably according to the invention, compound (B2) comprises three hydroxyl groups. More preferably according to the invention, compound (B2) is chosen among glycerol, pentaerythritol and combinations thereof.

Also particularly preferably according to the invention, compound (B3) comprises three hydroxyl groups. More preferably according to the invention, compound (B3) is chosen among polyethoxylated glycerol, polyethoxylated pentaerythritol and combinations thereof.

Also particularly preferably according to the invention, compound (B4) is a compound of formula (chem II) wherein Q independently represents a straight or branched $C_8$-$C_{22}$-alkyl group or a straight or branched $C_{12}$-$C_{22}$-alkyl group, more preferentially a straight or branched Cis-alkyl group. More preferably according to the invention, compound (B4) is a compound of formula (chem II) wherein Q independently represents a straight $C_8$-$C_{22}$-alkyl group or a straight $C_{12}$-$C_{22}$-alkyl group, more preferably a straight Cis-alkyl group. Particularly preferably, Q independently represents a straight alkyl group.

Preferably according to the invention, the monoisocyanate compound (C1) comprises a single isocyanate group. According to the invention, the monoisocyanate compound (C1) can be prepared by a separate reaction:
  of at least one compound comprising at least one labile hydrogen atom and
  of at least one diisocyanate compound, preferably an asymmetric diisocyanate compound, of at least one polyisocyanate compound, and combinations thereof.

Preferably according to the invention, the monohydroxyl compound (C2) comprises a single hydroxyl group. More preferably according to the invention, the monohydroxyl compound (C2) is chosen among a $C_6$-$C_{22}$ alcohol, preferably a $C_8$-$C_{18}$ alcohol, a $C_{12}$-$C_{16}$ alcohol and combinations thereof.

Preferably according to the invention, the polyurethane compound (a1) can also be a polyurethane compound (a1-2) prepared in the absence of any diisocyanate compound, by reaction:
of at least one polyisocyanate compound (A2);
of at least one polyhydroxyl compound (B), preferably chosen among:
a compound (B1) of formula (chem I):

(HO)-L$_n$-(OH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

HO—(OA)$_p$N(Q)-(OA)$_q$-OH wherein Q independently represents a straight or branched C$_8$-C$_{32}$-alkyl group, OA independently represents an ethoxylated group or a combination of ethoxylated groups (—CH$_2$CH$_2$O—) and propoxylated groups (—CH$_2$C(CH$_3$)O—) and p and q independently represent a number ranging from 50 to 200;
their combinations; and
of at least one compound (C) chosen among a monoisocyanate compound (C1), a monohydroxyl compound (C2) and combinations thereof.
Preferably according to the invention, the polyurethane-polyurea compound (a2) is prepared by reaction:
of at least one isocyanate compound (A) independently chosen among a diisocyanate compound (A1), a polyisocyanate compound (A2) and combinations thereof;
of at least one polyhydroxyl compound (B), preferably chosen among:
a compound (B1) of formula (chem I):

(HO)-L$_n$-(OH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

HO—(OA)$_p$N(Q)-(OA)$_q$-OH wherein Q independently represents a straight or branched C$_8$-C$_{32}$-alkyl group, OA independently represents an ethoxylated group or a combination of ethoxylated (—CH$_2$CH$_2$O—) groups and propoxylated (—CH$_2$C(CH$_3$)O—) groups and p and q independently represent a number ranging from 50 to 200;
combinations thereof;
of at least one diamine compound (D), preferably independently chosen among:
a compound (D1) of formula (chem III):

(H$_2$N)-T$_m$-(NH$_2$)

wherein T independently represents a poly(alkylene glycol) residue or a C$_4$-C$_{20}$-alkylene group, and m independently represents a number ranging from 40 to 400; optionally in combination with a polyamine compound;

a compound (D2) of formula (chem IV):

(H(R$^1$)N)-T$_m$-(NH$_2$)

wherein T independently represents a poly(alkylene glycol) residue or a C$_4$-C$_{20}$-alkylene group, m independently represents a number ranging from 40 to 400 and R$^1$ independently represents a straight or branched C$_1$-C$_{12}$-alkyl group; optionally in combination with a polyamine compound, preferably with a triamine compound;
a compound (D3) of formula (chem V):

(H(R$^1$)N)-T$_m$-(N(R$^2$)H)

wherein T independently represents a poly(alkylene glycol) residue or a C$_4$-C$_2$O-alkylene group, m independently represents a number ranging from 40 to 400 and R$^1$ and R$^2$, identical or different, independently represents a straight or branched C$_1$-C$_{12}$-alkyl group; optionally in combination with a polyamine compound, preferably with a triamine compound;
combinations thereof; and
of at least one compound (E) independently chosen among a monoisocyanate compound (E1), a monoamine compound (E2) and combinations thereof.
Preferably according to the invention, compound (D) is a compound (D1) according to the invention.
Preferably according to the invention, the monoisocyanate compound (E1) comprises a single isocyanate group. According to the invention, the monoisocyanate compound (E1) can be prepared by a separate reaction
of at least one compound comprising at least one labile hydrogen atom and
of at least one diisocyanate compound, preferably an asymmetric diisocyanate compound, of at least one polyisocyanate compound, and combinations thereof.
Preferably according to the invention, the monoamine compound (E2) comprises a single amine group, preferably a single primary amine group or a single secondary amine group.
Also more preferably according to the invention, compound (E2) is a compound of formula (chem VI).

T$^1$(T$^2$)N—(OE)$_r$-OH wherein T$^1$ and T$^2$ independently represent a straight or branched C$_8$-C$_{18}$-alkyl group, preferably T$^1$ and T$^2$ independently represent a straight or branched C$_8$-C$_{18}$-alkyl group, EO independently represents an ethoxylated group and r independently represents a number ranging from 3 to 150, preferably a number ranging from 3 to 100.
More preferably according to the invention, compound (E2) is chosen among octyl-N-amine, decyl-N-amine, undecenyl-N-amine, dodecyl-N-amine and mixtures thereof.
Preferably according to the invention, the polyether compound (a3) is prepared by reaction
of at least one polyhydroxyl compound (B), preferably chosen among:
a compound (B1) of formula (chem I):

(HO)-L$_n$-(OCH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups; preferably chosen among polyethoxylated glycerol, polyethoxylated pentaerythrithol, polyethoxylated sorbitol, in particular chosen among polyethoxylated glycerol with a molecular weight greater than 2,000 g/mol or greater than 4,000 g/mol, polyethoxylated pentaerythrithol with a molecular weight greater than 2,000 g/mol or greater than 4,000 g/mol, polyethoxylated sorbitol with a molecular weight greater than 2,000 g/mol or greater than 4,000 g/mol;

a compound (B4) of formula (chem II):

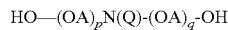

HO—(OA)$_p$N(Q)-(OA)$_q$-OH wherein Q independently represents a straight or branched $C_8$-$C_{32}$-alkyl group, OA independently represents an ethoxylated group or a combination of ethoxylated (—CH$_2$CH$_2$O—) groups and propoxylated (—CH$_2$C(CH$_3$)O—) groups and p and q independently represent a number ranging from 50 to 200;

combinations thereof; and of at least one compound comprising at least one halide group (F).

Preferably according to the invention, compound (F) is chosen among a monohalide compound (F1) alone or in combination with a polyhalide compound (F2), a polyhalide compound (F2) and combinations thereof, more particularly a combination of a monohalide compound (F1) and a polyhalide compound (F2).

Also preferably according to the invention, compound (F) is chosen among a straight alkyl halide, a branched alkyl halide, a cycloalkyl halide, a straight alkenyl halide, a branched alkenyl halide, and a cycloalkenyl halide, an alkenyl halide, and combinations thereof. Preferably, it is chosen among a straight alkyl halide, an aromatic alkenyl halide and combinations thereof. More preferably according to the invention, compound (F) is chosen among a monohalide compound (F1), a polyhalide compound (F2) and combinations thereof.

Preferably according to the invention, the polyhalide compound (F2) comprises from 2 to 5 halide groups. More preferably according to the invention, the polyhalide compound (F2) is a dihalide, a trihalide, or a tetrahalide.

Also more preferably according to the invention, the halide compound (F) is an iodide, a bromide or a chloride, much more preferentially a bromide. The preferred polyhalide compounds (F) according to the invention are chosen among:

a straight $C_1$-$C_{22}$-alkyl halide, a straight $C_1$-$C_{18}$-alkyl halide, a straight $C_1$-$C_{12}$-alkyl halide,
a branched $C_1$-$C_{22}$-alkyl halide, a branched $C_1$-$C_{18}$-alkyl halide, a branched $C_1$-$C_{12}$-alkyl halide,
a $C_5$-$C_7$-cycloalkyl halide,
a straight $C_1$-$C_{22}$-alkenyl halide, a straight $C_1$-$C_{18}$-alkenyl halide, a straight $C_1$-$C_{12}$-alkenyl halide,
a branched $C_1$-$C_{22}$-alkenyl halide, a branched $C_1$-$C_{18}$-alkenyl halide, a branched $C_1$-$C_{12}$-alkenyl halide,
a $C_5$-$C_7$-cycloalkenyl halide,
an aromatic $C_5$-$C_7$-alkenyl halide,
and combinations thereof.

The more preferred polyhalide compounds (F2) according to the invention are chosen among:

a straight $C_1$-$C_{12}$ alkyl polyhalide, preferably a straight $C_1$-$C_{12}$-alkyl polyhalide, in particular a straight α,ω-$C_1$-$C_{12}$-alkyl dihalide, in particular a straight α,ω-$C_1$-$C_{12}$-alkyl dibromide, in particular dibromomethane,
an aromatic $C_5$-$C_7$-alkenyl polyhalide, preferably an aromatic $C_5$-$C_7$-alkenyl dihalide, particularly 1,3-(dibromomethylene)phenyl,
and combinations thereof.

More preferably according to the invention, compound (F) is chosen among a monobromide compound (F1a), alone or in combination with a dibromide compound (F2a), and combinations thereof, more particularly a combination of a compound (F1a) and a compound (F2a).

Preferably according to the invention, the polyester compound (a4) is prepared by reaction of at least one polyhydroxyl compound (B), preferably chosen among:
a compound (B1) of formula (chem I):

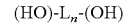

(HO)-L$_n$-(OH)

wherein L independently represents a poly(alkylene glycol) residue and n independently represents a number ranging from 40 to 400;

a compound (B1) of formula (chem I) combined with a non-alkoxylated compound (B2) comprising at least three hydroxyl groups;
a polyalkoxylated compound (B3) comprising at least three hydroxyl groups; preferably chosen among polyethoxylated glycerol, polyethoxylated pentaerythrithol, polyethoxylated sorbitol;
a compound (B4) of formula (chem II):

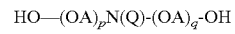

HO—(OA)$_p$N(Q)-(OA)$_q$-OH wherein Q independently represents a straight or branched $C_8$-$C_{32}$-alkyl group, OA independently represents an ethoxylated (—CH$_2$CH$_2$O—) group or a combination of ethoxylated (—CH$_2$CH$_2$O—) groups and propoxylated (—CH$_2$C(CH$_3$)O—) groups and p and q independently represent a number ranging from 50 to 200;

combinations thereof; and of at least one compound comprising at least one carboxylic acid group (G); preferably chosen among a diacid compound (G1), a monocarboxylic acid compound (G2), an acid chloride (G3) and combinations thereof, in particular chosen among a diacid compound (G1), a monocarboxylic acid compound (G2), an acid chloride (G3).

Preferably according to the invention, compound (G) is therefore a fatty acid. More preferably according to the invention, compound (G) comprises at least one straight or branched $C_8$-$C_{22}$-alkyl group or one straight or branched $C_{12}$-$C_{22}$-alkyl group, more preferably one straight or branched $C_{18}$-alkyl group.

Preferably according to the invention, compound (G1) is a fatty carboxylic diacid. More preferably according to the invention, compound (G1) is a dicarboxylic acid comprising at least one straight or branched $C_8$-$C_{22}$-alkyl group or a straight or branched $C_{12}$-$C_{22}$-alkyl group, more preferably a straight or branched $C_{18}$-alkyl group.

Also preferably according to the invention, compound (G2) is a fatty carboxylic monoacid. More preferably according to the invention, compound (G2) is a monocarboxylic acid comprising at least one straight or branched $C_8$-$C_{22}$-alkyl group or a straight or branched $C_{12}$-$C_{22}$-alkyl group, more preferably a straight or branched Cis-alkyl group.

Preferably according to the invention, compound (G) is a combination of at least one diacid compound (G1) and at least one monocarboxylic acid compound (G2). Also preferably according to the invention, compound (G) is a combination of at least one diacid compound (G1) and at least one monocarboxylic acid compound (G2).

Preferably according to the invention, the polyurea compound (a5) is prepared by reaction
of at least one isocyanate compound (A) independently chosen among a diisocyanate compound (A1), a polyisocyanate compound (A2) and combinations thereof;
of at least one diamine compound (D), preferably independently chosen among:
a compound (D1) of formula (chem III):

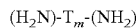

wherein T independently represents a poly(alkylene glycol) residue and m independently represents a number ranging from 40 to 400; optionally in combination with a polyamine compound, preferably a triamine compound;
a compound (D2) of formula (chem IV):
More preferably according to the invention, the monoisocyanate compounds are independently chosen among:
aromatic monoisocyanate compounds, in particular phenyl isocyanate, diphenyl methane monoisocyanate, 2-phenylethyl isocyanate, 4-tolyl isocyanate, 2-tolyl isocyanate, 2,5-dimethylphenyl isocyanate, 3,4-dimethylphenyl isocyanate, 2,3-dimethylphenyl isocyanate, 4-isocyanato-4'-methyldiphenyl methane;
polyfunctional aromatic monoisocyanate compounds, in particular 2-methoxy-4-nitrophenyl isocyanate; polymethylene polyphenyl isocyanate;
the alkyl monoisocyanate compounds, in particular hexyl isocyanate, heptyl isocyanate, octyl isocyanate, n-nonyl isocyanate, decyl isocyanate, undecyl isocyanate, dodecyl isocyanate, tridecyl isocyanate, tetradecyl isocyanate, cetyl isocyanate, 2-ethylhexyl isocyanate, n-octyl isocyanate, isononyl isocyanate, stearyl isocyanate, decyl isocyanate, undecyl isocyanate, dodecyl isocyanate, tridecyl isocyanate, tetradecyl isocyanate, cetyl isocyanate, behenyl isocyanate, lignoceryl isocyanate, cerotyl isocyanate, eicosanyl isocyanate;
the cycloalkyl monoisocyanate compounds, in particular cyclohexyl isocyanate, 1-isocyanatomethyl-1,3,3-trimethylcyclohexane.
Preferably according to the invention, the diisocyanate compounds are independently chosen among:
symmetric aromatic diisocyanate compounds, preferably:
2,2'-methylene diphenyl diisocyanate (2,2'-MDI) and
4,4'-methylene diphenyl diisocyanate (4,4'-MDI);
4,4'-dibenzyl diisocyanate (4,4'-DBDI);
2,6-toluene diisocyanate (2,6-TDI);
m-xylylene diisocyanate (m-XDI);
symmetric alicyclic diisocyanate compounds, preferably bis(4-cyclohexylisocyanate) methylene (H12MDI);
symmetric aliphatic diisocyanates, preferably hexamethylene diisocyanate (HDI), pentamethylene diisocyanate (PDI);
asymmetric aromatic diisocyanates, preferably:
2,4'-methylene diphenyl diisocyanate (2,4'-MDI);
2,4'-dibenzyl diisocyanate (2,4'-DBDI);
2,4-toluene diisocyanate (2,4-TDI):
a biuret trimer compound, in particular a biuret trimer compound of a compound chosen among:
symmetric aromatic diisocyanate compounds, preferably:
2,2'-methylene diphenyl diisocyanate (2,2'-MDI) and
4,4'-methylene diphenyl diisocyanate (4,4'-MDI);
4,4'-dibenzyl diisocyanate (4,4'-DBDI);
2,6-toluene diisocyanate (2,6-TDI);
m-xylylene diisocyanate (m-XDI);
symmetric alicyclic diisocyanate compounds, preferably bis(4-cyclohexylisocyanate) methylene (H12MDI);
symmetric aliphatic diisocyanate compounds, preferably hexamethylene diisocyanate (HDI), pentamethylene diisocyanate (PDI);
asymmetric aromatic diisocyanate compounds, preferably:
2,4'-methylene diphenyl diisocyanate (2,4'-MDI);
2,4'-dibenzyl diisocyanate (2,4'-DBDI);
2,4-toluene diisocyanate (2,4-TDI);
asymmetric alicyclic diisocyanate compounds, preferably isophorone diisocyanate (IPDI);
asymmetric aromatic diisocyanate compounds, preferably 2,4'-methylene diphenyl diisocyanate (2,4'-MDI), 2,4'-dibenzyl diisocyanate (2,4'-DBDI), 2,4-toluene diisocyanate (2,4-TDI);
asymmetric alicyclic diisocyanate compounds, preferably isophorone diisocyanate (IPDI).
More preferably according to the invention, the polyisocyanate compounds are independently chosen among:
triphenylmethane-4,4',4''-triisocyanate;
1,1',1''-methylidynetris (4-isocyanatobenzene);
an isocyanurate compound, in particular an isocyanurate compound of a compound chosen among:
symmetric aromatic diisocyanate compounds, preferably:
2,2'-methylene diphenyl diisocyanate (2,2'-MDI) and
4,4'-methylene diphenyl diisocyanate (4,4'-MDI);
4,4'-dibenzyl diisocyanate (4,4'-DBDI);
2,6-toluene diisocyanate (2,6-TDI);
m-xylylene diisocyanate (m-XDI);
symmetric alicyclic diisocyanate compounds, preferably bis(4-cyclohexylisocyanate) methylene (H12MDI);
symmetric aliphatic diisocyanate compounds, preferably hexamethylene diisocyanate (HDI), pentamethylene diisocyanate (PDI);
asymmetric aromatic diisocyanate compounds, preferably:
2,4'-methylene diphenyl diisocyanate (2,4'-MDI);
2,4'-dibenzyl diisocyanate (2,4'-DBDI);
2,4-toluene diisocyanate (2,4-TDI);
a biuret trimer compound, in particular a biuret trimer compound of a compound chosen among:
symmetric aromatic diisocyanate compounds, preferably:
2,2'-methylene diphenyl diisocyanate (2,2'-MDI) and
4,4'-methylene diphenyl diisocyanate (4,4'-MDI);
4,4'-dibenzyl diisocyanate (4,4'-DBDI);
2,6-toluene diisocyanate (2,6-TDI);
m-xylylene diisocyanate (m-XDI);
symmetric alicyclic diisocyanate compounds, preferably bis(4-cyclohexylisocyanate) methylene (H12MDI);
symmetric aliphatic diisocyanate compounds, preferably hexamethylene diisocyanate (HDI), pentamethylene diisocyanate (PDI);
asymmetric aromatic diisocyanate compounds, preferably:
2,4'-methylene diphenyl diisocyanate (2,4'-MDI);
2,4'-dibenzyl diisocyanate (2,4'-DBDI);
2,4-toluene diisocyanate (2,4-TDI);
alicyclic diisocyanate compounds, preferably isophorone diisocyanate (IPDI).
According to the invention, the compounds comprising at least one labile hydrogen atom comprise at least one hydrogen atom that is reactant with a compound comprising at least one isocyanate group (—N=C=O). Preferably, the compounds comprising at least one labile hydrogen atom are chosen among a compound comprising at least one (—OH) hydroxyl group; a compound comprising a primary (—NH$_2$) amine group or a secondary (—N(H)—) amine group; preferably a compound comprising a hydroxyl group, including a mono-alcohol, for example a straight, branched or cyclic $C_6$-$C_{40}$ or $C_5$-$C_{36}$ mono-alcohol, preferably $C_{10}$-$C_{32}$, more preferentially $C_{12}$-$C_{30}$, in particular $C_{12}$ or $C_{18}$ or $C_{21}$ or $C_{30}$. The various thickening compounds (a), in particular the polyurethane compound (a1), the polyurethane-polyurea compound (a2), the polyether compound (a3), the polyester compound (a4) and the polyurea compound (a5), are generally known as such. They can be prepared by preparation methods used in the prior art.

In addition to water and at least one compound (a), the composition according to the invention also comprises at least one non-ionic compound (b) comprising at least one hydrophilic osidic group bound to at least one straight or branched hydrophobic chain. Preferably according to the invention, the non-ionic compound (b) comprises at least one straight or branched hydrophobic chain comprising from 4 to 14 carbon atoms, preferably from 5 to 12 or from 4 to 10 or from 4 to 8 or from 6 to 9 carbon atoms, in particular 5, 6, 7, 8 or 10 carbon atoms. Also preferably according to the invention, the non-ionic compound (b) is non-alkoxylated, particularly non-ethoxylated.

Generally according to the invention, the non-ionic compound (b) has a molecular weight of less than 5,000 g/mol. Preferably according to the invention, the non-ionic compound (b) has a molecular weight of less than 1,000 g/mol.

Also preferably according to the invention, the non-ionic compound (b) is chosen among non-substituted sugar esters (non-substituted sucroesters), non-substituted sugar ethers (non-substituted sucroethers) and combinations thereof.

According to the invention, the non-ionic compound (b) can comprise one or more osidic cycles. According to the invention, the non-ionic compound (b) does not comprise any cyclodextrin or any cyclodextrin derivative. Also according to the invention, the non-ionic compound (b) is different from a cyclodextrin or a cyclodextrin-derived compound.

The non-ionic compound (b) comprises at least one straight or branched hydrophobic chain bound to the hydrophilic osidic group. Preferably according to the invention, the straight or branched hydrophobic chain comprises 5, 6, 7, 8, 10 or 12 carbon atoms. More preferably according to the invention, the straight or branched hydrophobic chain comprises 5, 6, 7, 8 or 10 carbon atoms.

The non-ionic compound (b) according to the invention also comprises at least one hydrophilic osidic group bound to at least one hydrophobic chain. It can be prepared from different compounds comprising at least one hydrophilic osidic group that can bind to a compound comprising at least one hydrophobic chain. For example, the non-ionic compound (b) according to the invention can be prepared from a compound chosen among an ose (b1) comprising from 3 to 8 carbon atoms, a ose oligomer (b2) comprising from 1 to 5 ose units, a product (b3) resulting from the degradation of a saccharide.

Derivative (b1) is an ose that comprises a free hemiacetal group or a hemicetal group condensed between the hydroxyl of the hemiacetal group carried by the anomeric carbon and an OH group of another molecule. This ose (b1) can be chosen among trioses (oses comprising 3 carbon atoms), tetroses (oses comprising 4 carbon atoms), pentoses (oses comprising 5 carbon atoms), hexoses and deoxyhexoses (oses comprising 6 carbon atoms), heptoses (oses comprising 7 carbon atoms), octoses (oses comprising 8 carbon atoms). It can be chosen among glyceraldehyde, dihydroxyacetone, erythrose, threose, erythrulose, deoxyribose, ribose, arabinose, xylose, lyxose, ribulose, xylulose, alloxyribose, altrose, galactose, glucose, gulose, idose, mannose, talose, fructose, psicose, sorbose, tagatose, fucose, rhamnose, sedoheptulose, mannoheptulose, heptahydroxyoctanal. Preferably, glucose is used alone or in a mixture.

Derivative (b2) is an oligomer formed from a defined number of oses. It can be chosen among ose dimers, ose trimers, and ose tetramers. It can also be chosen among dextrose, maltose, lactose, sucrose, maltoriose, maltotetraose, alpha-glucoheptonic acid, beta-glucoheptonic acid and combinations thereof. Preferably, sucrose is used alone or in a mixture.

Derivative (b3) is a product resulting from the degradation of a saccharide generally obtained from a ketose that is degraded under defined conditions, leading to a chain rupture at the level of the ketone group. The product (b3) can be chosen among aldoses, synthetic monosaccharide derivatives and synthetic disaccharide derivatives. More preferentially, it is chosen among sorbitol derivatives, mannitol derivatives, their mixtures and combinations thereof.

More preferably according to the invention, the non-ionic compound (b) is chosen among:
 the unsubstituted sugar monoesters,
 the non-substituted sugar diesters,
 the unsubstituted sugar monoethers,
 the unsubstituted sugar diethers,
 and combinations thereof.

Also preferably according to the invention, the non-ionic compound (b) is obtained by reaction
 of a compound comprising at least one hydrophilic osidic group chosen among fructose, galactose, glucose, lactose, maltose, sucrose, sorbitan, sorbitol and combinations thereof; and
 of a compound comprising a hydrophobic chain chosen among the fatty acids, preferably the acids in which the hydrophobic chain comprises from 4 to 10 carbon atoms, for example adipic acid, pentanoic acid, hexanoic acid, heptaoic acid, octanoic acid and combinations thereof, preferably pentanoic acid, hexanoic acid, heptaoic acid, octanoic acid and combinations thereof.

Also preferably according to the invention, the non-ionic compound (b) is obtained
 by esterification from a compound comprising at least one hydrophilic osidic group and a hydroxyl group and from a compound comprising a hydrophobic chain and at least one carboxylic group, or
 by transesterification from a compound comprising at least one hydrophilic osidic group and an ester group and from a compound comprising a hydrophobic chain and at least one different ester group, or
 by condensing a compound comprising at least one hydrophilic osidic group with a compound comprising a hydrophobic chain and a starting group.

Also preferably according to the invention, the non-ionic compound (b) is chosen among oside hexyl ester, oside heptyl ester, oside octyl ester and combinations thereof, preferably sucrose hexyl ester, sucrose heptyl ester, sucrose octyl ester and combinations thereof;
 oside hexyl ether, oside heptyl ether, oside octyl ether and combinations thereof, preferably sucrose hexyl ether, sucrose heptyl ether, sucrose octyl ether and combinations thereof; and
 combinations thereof.

The composition according to the invention can be prepared according to different methods. Preferably, the composition according to the invention is prepared by mixing the different ingredients, in particular by mixing water and compounds (a) and (b). Also preferably, this mixture is performed under stirring.

The composition according to the invention has particularly useful properties. In particular, the composition according to the invention is very useful for controlling the viscosity of the medium in which it is used, in particular for controlling the viscosity of an aqueous formulation.

Thus, the invention also relates to a method for controlling the viscosity of an aqueous formulation comprising the addition of at least one composition according to the invention in this formulation. This method according to the invention can also be implemented by introducing into an aqueous formulation at least one combination of the compounds (a) and (b) defined according to the invention.

Particularly advantageously, the efficacy of the viscosity control method according to the invention is not dependent on the pH variations of the aqueous formulation. Thus, controlling the viscosity by means of the composition according to the invention, or by means of a combination of the compounds (a) and (b) defined according to the invention, is effective for pH variations of the aqueous formulation ranging from pH 5 to pH 12 or from pH 6 to pH 9.

Preferably, the viscosity control method according to the invention is used to control the viscosity of an aqueous formulation chosen among a paint formulation, a varnish formulation, an adhesive formulation, a render coating formulation, a filler formulation, a grout formulation, a tincture formulation, an ink formulation, a coating paper formulation, a detergent formulation, a cosmetic formulation, comprising at least one aqueous composition according to the invention or at least one combination of compounds (a) and (b) defined according to the invention, and at least one compound chosen among a pigment, a binder, a latex, a solvent, a detergent compound, a cosmetic compound, an adhesive compound and combinations thereof, preferably a combination of a pigment and a binder or a combination of a pigment and a latex.

Advantageously, the aqueous composition according to the invention can be used directly. It can also be used indirectly by incorporating it into a formulation comprising other ingredients.

Thus, the invention provides an aqueous formulation comprising at least one aqueous composition according to the invention and at least one compound chosen among a pigment, a binder, a latex, a solvent, a detergent compound, a cosmetic compound, an adhesive compound. Preferably, the formulation according to the invention is chosen among a paint formulation, a varnish formulation, an adhesive formulation, a render coating formulation, a filler formulation, a grout formulation, a tincture formulation, an ink formulation, a coating paper formulation, a detergent formulation, a cosmetic formulation; it comprises at least one composition according to the invention or at least one combination of the compounds (a) and (b) defined according to the invention, and at least one compound chosen among a pigment, a binder, a latex, a solvent, a detergent compound, a cosmetic compound, an adhesive compound.

The use of the composition according to the invention therefore makes it possible to prepare an aqueous formulation having improved properties. Thus, the invention also relates to the preparation of a formulation chosen among a paint formulation, a varnish formulation, an adhesive formulation, a render coating formulation, a filler formulation, a grout formulation, a tincture formulation, an ink formulation, a coating paper formulation, a detergent formulation, a cosmetic formulation. Preferably, the invention relates to the preparation of a formulation chosen among a paint formulation, a varnish formulation, a detergent formulation and a cosmetic formulation.

The following examples illustrate the various aspects of the invention.

EXAMPLE 1: PREPARATION OF COMPOSITIONS ACCORDING TO THE INVENTION

Preparation of the Composition According to the Invention (C1)

In a 3 L glass reactor equipped with a mechanical stirring rod, vacuum pump, and nitrogen inlet, and heated by means of a jacket in which oil circulates, 316.3 g of polyethylene glycol having a molecular mass ($M_w$) of 10,000 g/mol (PEG 10,000) is introduced along with 13.5 g of docecan-1-ol. This stirred medium is heated to 100° C. and nitrogen is allowed to bubble. After one hour, 500 ppm of a bismuth carboxylate-type catalyst is added, then, after homogenisation of the medium, 14.8 g of isophorone diisocyanate (IPDI) is added. The reaction is allowed to continue for 1 hour.

Then, we check that the NCO group rate is zero.

At the end of the reaction, 246 g of a non-ionic compound resulting from glucose condensation with n-heptanol (Simulsol SL7G, Seppic) is added. This mixture is stirred for 30 minutes. Then, 1,000 ppm of biocidal agent (CMIT/MIT), 500 ppm of defoamer (Tego 1488, Evonik) and the appropriate amount of hot water are added to achieve a composition having a solids content of 30% by weight.

Preparation of the Composition According to the Invention (C2)

In a 3 L glass reactor equipped with a mechanical stirring rod, vacuum pump, and nitrogen inlet, and heated by means of a jacket in which oil circulates, 315.2 g of polyethylene glycol having a molecular mass ($M_w$) of 10,000 g/mol (PEG 10,000) is introduced along with 17.2 g of dodecylcyclohexanol and 8.0 g of dodecan-1-ol. This stirred medium is heated to 100° C. and nitrogen is allowed to bubble. After one hour, 500 ppm of a bismuth carboxylate-type catalyst is added, then, after homogenisation of the medium, 23.7 g of isophorone diissocyanate (IPDI) is added. The reaction is allowed to continue for 1 hour.

Then, we check that the NCO group rate is zero.

At the end of the reaction, 260 g of a non-ionic compound resulting from glucose condensation with n-heptanol (Simulsol SL7G, Seppic) is added. This mixture is stirred for 30 minutes. Then, 1,000 ppm of biocidal agent (CMIT/MIT), 500 ppm of defoamer (Tego 1488, Evonik) and the appropriate amount of hot water are added to achieve a composition having a solids content of 30% by weight.

Preparation of the Composition According to the Invention (C3)

In a 3 L glass reactor equipped with a mechanical stirring rod, vacuum pump, and nitrogen inlet, and heated by means of a jacket in which oil circulates, 315.5 g of polyethylene glycol having a molecular mass ($M_w$) of 10,000 g/mol (PEG 10000) is introduced along with 34.9 g of ethoxylated tristyrylphenol having 5 ethylene oxide units. This stirred medium is heated to 100° C. and nitrogen is allowed to bubble. After one hour, 500 ppm of a bismuth carboxylate-type catalyst is added, then, after homogenisation of the medium, 23.7 g of isophorone diisocyanate (IPDI) is added. The reaction is allowed to continue for 1 hour.

Then, we check that the NCO group rate is zero.

At the end of the reaction, 267 g of a non-ionic compound resulting from glucose condensation with n-heptanol (Simulsol SL7G, Seppic) is added. This mixture is stirred for 30 minutes. Then, 1,000 ppm of biocidal agent (CMIT/MIT), 500 ppm of defoamer (Tego 1488, Evonik) and the appropriate amount of hot water are added to achieve a composition having a solids content of 30% by weight.

Preparation of a Composition According to the Invention (C4)

In a 3 L glass reactor equipped with a mechanical stirring rod, vacuum pump, and nitrogen inlet, and heated by means of a jacket in which oil circulates, 315.4 g of polyethylene glycol having a molecular mass (Mu) of 10,000 g/mol (PEG 10,000) is introduced along with 31.0 g of ethoxylated cardanol having 5 ethylene oxide units. This stirred medium is heated to 100° C. and nitrogen is allowed to bubble. After one hour, 500 ppm of a bismuth carboxylate-type catalyst is added, then, after homogenisation of the medium, 16.7 g of isophorone diisocyanate (IPDI) is added.

The reaction is allowed to continue for 1 hour.

Then, we check that the NCO group rate is zero.

At the end of the reaction, 259 g of a non-ionic compound resulting from glucose condensation with a blend of n-heptanol and n-decanol (Simulsol SL8, Seppic) is added. This mixture is stirred for 30 minutes. Then, 1,000 ppm of biocidal agent (CMIT/MIT), 500 ppm of defoamer (Tego 1488, Evonik) and the appropriate amount of hot water are added to achieve a composition having a solids content of 30% by weight.

EXAMPLE 2: PREPARATION OF COMPARATIVE COMPOSITIONS

Preparation of the Comparative Composition (CC1)

In a 3 L glass reactor equipped with a mechanical stirring rod, vacuum pump, and nitrogen inlet, and heated by means of a jacket in which oil circulates, 316.3 g of polyethylene glycol having a molecular mass (Mw) of 10,000 g/mol (PEG 10,000) is introduced along with 13.5 g of docecan-1-ol. This stirred medium is heated to 100° C. and nitrogen is allowed to bubble. After one hour, 500 ppm of a bismuth carboxylate-type catalyst is added, then, after homogenisation of the medium, 14.8 g of isophorone diisocyanate (IPDI) is added. The reaction is allowed to continue for 1 hour.

Then, we check that the NCO group rate is zero. To do this, 1 g is collected from the reaction medium to which an excess of dibutylamine (1 molar) is added that reacts with the isocyanate groups present in the medium. The unreacted dibutylamine is then dosed with hydrochloric acid (1 N). The number of isocyanate groups present in the reaction medium can then be deduced.

At the end of the reaction, 1,000 ppm of biocidal agent (CMIT/MIT), 500 ppm of defoamer (Tego 1488, Evonik) and the appropriate amount of hot water are added to achieve a composition having a solids content of 17.5% by weight.

Preparation of the Comparative Composition (CC2)

In a 3 L glass reactor equipped with a mechanical stirring rod, vacuum pump, and nitrogen inlet, and heated by means of a jacket in which oil circulates, 315.2 g of polyethylene glycol having a molecular mass ($M_w$) of 10,000 g/mol (PEG 10,000) is introduced along with 17.2 g of dodecylcyclohexanol and 8.0 g of dodecan-1-ol. This stirred medium is heated to 100° C. and nitrogen is allowed to bubble. After one hour, 500 ppm of a bismuth carboxylate-type catalyst is added, then, after homogenisation of the medium, 23.7 g of isophorone diisocyanate (IPDI) is added. The reaction is allowed to continue for 1 hour.

Then, we check that the NCO group rate is zero.

At the end of the reaction, 1,000 ppm of biocidal agent (CMIT/MIT), 500 ppm of defoamer (Tego 1488, Evonik) and the appropriate amount of hot water are added to achieve a composition having a solids content of 17.5% by weight.

Preparation of the Comparative Composition (CC3)

In a 3 L glass reactor equipped with a mechanical stirring rod, vacuum pump, and nitrogen inlet, and heated by means of a jacket in which oil circulates, 315.2 g of polyethylene glycol having a molecular mass ($M_w$) of 10,000 g/mol (PEG 10,000) is introduced along with 34.9 g of ethoxylated tristyrylphenol having 5 ethylene oxide units. This stirred medium is heated to 100° C. and nitrogen is allowed to bubble. After one hour, 500 ppm of a bismuth carboxylate-type catalyst is added, then, after homogenisation of the medium, 23.7 g of isophorone diisocyanate (IPDI) is added.

The reaction is allowed to continue for 1 hour.

Then, we check that the NCO group rate is zero as explained above.

At the end of the reaction, 1,000 ppm of biocidal agent (CMIT/MIT), 500 ppm of defoamer (Tego 1488, Evonik) and the appropriate amount of hot water are added to achieve a composition having a solids content of 17.5% by weight.

Preparation of the Comparative Composition (CC4)

In a 3 L glass reactor equipped with a mechanical stirring rod, vacuum pump, and nitrogen inlet, and heated by means of a jacket in which oil circulates, 315.4 g of polyethylene glycol having a molecular mass ($M_w$) of 10,000 g/mol (PEG 10,000) is introduced along with 31.0 g of ethoxylated cardanol having 5 ethylene oxide units. This stirred medium is heated to 100° C. and nitrogen is allowed to bubble. After one hour, 500 ppm of a bismuth carboxylate-type catalyst is added, then, after homogenisation of the medium, 16.7 g of isophorone diisocyanate (IPDI) is added.

The reaction is allowed to continue for 1 hour.

Then, we check that the NCO group rate is zero as explained above. At the end of the reaction, 1,000 ppm of biocidal agent (CMIT/MIT), 500 ppm of defoamer (Tego 1488, Evonik) and the appropriate amount of hot water are added to achieve a composition having a solids content of 17.5% by weight.

EXAMPLE 3: ASSESSMENT OF THE VISCOSITY OF THE COMPOSITIONS ACCORDING TO THE INVENTION AND THE COMPARATIVE COMPOSITIONS

The Brookfield viscosity at 25° C. and at 1 RPM with a No. 7 stirrer is measured for the compositions according to the invention. The Brookfield viscosity at 25° C. and at 1 rpm with a No. 6 stirrer is measured for the comparative compositions. The results are shown in Table 1.

| Composition | Viscosity (Pa · s) |
| --- | --- |
| C1 | 2.1 |
| C2 | 5.8 |
| C3 | 3.3 |

-continued

| Composition | Viscosity (Pa · s) |
|---|---|
| C4 | 12.5 |
| CC1 | 218 |
| CC2 | 697 |
| CC3 | 378 |
| CC4 | 3,500 |

These results show the very good efficacy of the combinations of compound (a) and of non-ionic compound (b) in the compositions according to the invention wherein the viscosity is much lower than the viscosity of the comparative compositions. The compositions according to the invention are highly concentrated and can be handled easily.

The invention claimed is:

1. An aqueous composition, comprising:
at least 40% by weight of water;
at least one polyalkoxylated compound (a) selected from the group consisting of a polyurethane compound (a1), a polyurethane-polyurea compound (a2), a polyether compound (a3), a polyester compound (a4), and a polyurea compound (a5); and
at least one non-ionic compound (b) comprising at least one hydrophilic osidic group bound to at least one straight or branched hydrophobic chain having 4 to 9 carbon atoms.

2. The aqueous composition according to claim 1, wherein the dry/dry weight ratio (a/b) of the quantities of the compound (a) and of the compound (b) ranges from 0.1 to 10.

3. The aqueous composition according to claim 1, wherein the compound (a) is a rheology-modifying compound; or compound (a) is a non-ionic compound, or an associative compound, or an associative non-ionic compound.

4. The aqueous composition according to claim 1, wherein the at least one polyalkoxylated compound (a) includes the polyurethane compound (a1), and the polyurethane compound (a1) is chosen among:
a polyurethane (a1-1) prepared by reaction:
of at least one isocyanate compound (A) independently chosen among a diisocyanate compound (A1), a polyisocyanate compound (A2), and combinations thereof;
of at least one polyhydroxyl compound (B) chosen among
a compound (B1) of formula (chem I):

(HO)-L$_n$-(OH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

HO—(OA)$_p$N(Q)-(OA)$_q$-OH wherein Q independently represents a straight or branched C$_8$-C$_{32}$-alkyl group, OA independently represents an ethoxylated group or a combination of ethoxylated (—CH$_2$CH$_2$O—) groups and propoxylated (—CH$_2$C(CH$_3$)O—) groups, and p and q independently represent a number ranging from 50 to 200; and
combinations thereof; and
of at least one compound (C) chosen among a monoisocyanate compound (C1), a monohydroxyl compound (C2), and combinations thereof;
a polyurethane (a1-2) prepared in the absence of any diisocyanate compound, by reaction:
of at least one polyisocyanate compound (A2);
of at least one polyhydroxyl compound (B) chosen among:
a compound (B1) of formula (chem I):

(HO)-L$_n$-(OH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

HO—(OA)$_p$N(Q)-(OA)$_q$-OH wherein Q independently represents a straight or branched C5-C32-alkyl group, OA independently represents an ethoxylated group or a combination of ethoxylated (—CH$_2$CH$_2$O—) groups and propoxylated (—CH$_2$C(CH$_3$)O—) groups, and p and q independently represent a number ranging from 50 to 200; and
combinations thereof; and
of at least one compound (C) chosen among a monoisocyanate compound (C1), a monohydroxyl compound (C2), and combinations thereof.

5. The aqueous composition according to claim 1, wherein the at least one polyalkoxylated compound (a) includes the polyurethane-polyurea compound (a2), and the polyurethane-polyurea compound (a2) is prepared by reaction:
of at least one isocyanate compound (A) independently chosen among a diisocyanate compound (A1), a polyisocyanate compound (A2), and combinations thereof;
of at least one polyhydroxyl compound (B) chosen among:
a compound (B1) of formula (chem I):

(HO)-L$_n$-(OH)

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

HO—(OA)$_p$N(Q)-(OA)$_q$-OH wherein Q independently represents a straight or branched C$_8$-C$_{32}$-alkyl group, OA independently represents an ethoxylated group or a combination of ethoxylated (—CH$_2$CH$_2$O—) groups and propoxylated (—CH$_2$C(CH$_3$)O—) groups, and p and q independently represent a number ranging from 50 to 200; and combinations thereof;
of at least one diamine compound (D) independently chosen among:
a compound (D1) of formula (chem III):

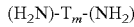

wherein T independently represents a poly(alkylene glycol) residue and m independently represents a number ranging from 40 to 400; optionally in combination with a polyamine compound;
a compound (D2) of formula (chem IV):
wherein T independently represents a poly(alkylene glycol) residue, or a $C_4$-$C_{20}$-alkylene group, m independently represents a number ranging from 40 to 400, and $R^1$ independently represents a straight or branched $C_1$-$C_{12}$-alkyl group; optionally in combination with a polyamine compound;
a compound (D3) of formula (chem V):

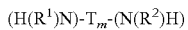

wherein T independently represents a poly(alkylene glycol) residue or a $C_4$-$C_{20}$-alkylene group, m independently represents a number ranging from 40 to 400 and $R^1$ and $R^2$, identical or different, independently represents a straight or branched $C_1$-$C_{12}$-alkyl group; optionally in combination with a polyamine compound; and
combinations thereof; and
of at least one compound (E) independently chosen among a monoisocyanate compound (E1), a monoamine compound (E2), and combinations thereof.

6. The aqueous composition according to claim 1, wherein the at least one polyalkoxylated compound (a) includes the polyether compound (a3), and the polyether compound (a3) is prepared by reaction:
of at least one polyhydroxyl compound (B) chosen among:
a compound (B1) of formula (chem I):

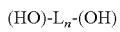

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

wherein Q independently represents a straight or branched $C_8$-$C_{32}$-alkyl group, OA independently represents an ethoxylated group or a combination of ethoxylated (—$CH_2CH_2O$—) groups and propoxylated (—$CH_2C(CH_3)$O—) groups, and p and q independently represent a number ranging from 50 to 200; and
combinations thereof; and
of at least one compound comprising at least one halide group (F).

7. The aqueous composition according to claim 1, wherein the at least one polyalkoxylated compound (a) includes the polyester compound (a4), and the polyester compound (a4) is prepared by polymerisation reaction:
of at least one polyhydroxyl compound (B) chosen among:
a compound (B1) of formula (chem I):

wherein L independently represents a poly(alkylene glycol) residue and n independently represents a number ranging from 40 to 400;
a compound (B1) of formula (chem I) combined with a non-alkoxylated compound (B2) comprising at least three hydroxyl groups;
a polyalkoxylated compound (B3) comprising at least three hydroxyl groups;
a compound (B4) of formula (chem II):

wherein Q independently represents a straight or branched $C_5$-$C_{32}$-alkyl group, OA independently represents an ethoxylated group or a combination of ethoxylated (—$CH_2CH_2O$—) groups and propoxylated (—$CH_2C(CH_3)$O—) groups, and p and q independently represent a number ranging from 50 to 200; and
combinations thereof; and
of at least one compound comprising at least one carboxylic acid group (G).

8. The aqueous composition according to claim 1, wherein the at least one polyalkoxylated compound (a) includes the polyurea compound (a5), and the polyurea compound (a) is prepared by reaction:
of at least one isocyanate compound (A) independently chosen among a diisocyanate compound (A1), a polyisocyanate compound (A2), and combinations thereof;
of at least one diamine compound (D), independently chosen among:
a compound (D1) of formula (chem III):

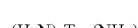

wherein T independently represents a poly(alkylene glycol) residue and m independently represents a number ranging from 40 to 400; optionally in combination with a polyamine compound;
a compound (D2) of formula (chem IV):

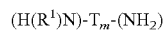

wherein T independently represents a poly(alkylene glycol) residue, m independently represents a number ranging from 40 to 400, and $R^1$ independently represents a straight or branched $C_1$-$C_{12}$-alkyl group; optionally in combination with a polyamine compound;
a compound (D3) of formula (chem V):
$(H(R^1)N)$-$T_m$-$(N(R^2)H)$
wherein T independently represents a poly(alkylene glycol) residue or a $C_4$-$C_{20}$-alkylene group, m independently represents a number ranging from 40 to 400 and $R^1$ and $R^2$, identical or different, independently represent a straight or branched $C_1$-$C_{12}$-alkyl group; optionally in combination with a polyamine compound; and
combinations thereof; and
of at least one compound (E) independently chosen among a monoisocyanate compound (E1), a monoamine compound (E3), and combinations thereof.

9. The aqueous composition according to claim 1, wherein the non-ionic compound (b) is chosen among non-substituted sugar esters, non-substituted sugar ethers, and combinations thereof.

10. The aqueous composition according to claim 1, wherein the non-ionic compound (b) is obtained by reaction:
of a compound comprising at least one hydrophilic osidic group chosen among fructose, galactose, glucose, lactose, maltose, sucrose, sorbitan, sorbitol, and combinations thereof; and of a compound comprising a hydrophobic chain chosen among fatty acids.

11. The aqueous composition according to claim 1, wherein the non-ionic compound (b) is chosen among:
   oside hexyl ester, oside heptyl ester, oside octyl ester and combinations thereof;
   oside hexyl ether, oside heptyl ether, oside octyl ether and combinations thereof; and
   combinations thereof.

12. The aqueous composition according to claim 1, wherein the non-ionic compound (b) is obtained:
   by esterification from a compound comprising at least one hydrophilic osidic group and a hydroxyl group and from a compound comprising a hydrophobic chain and at least one carboxylic group, or
   by transesterification from a compound comprising at least one hydrophilic osidic group and an ester group and from a compound comprising a hydrophobic chain and at least one different ester group, or
   by condensing a compound comprising at least one hydrophilic osidic group with a compound comprising a hydrophobic chain and a starting group.

13. An aqueous formulation, comprising at least one aqueous composition according to claim 1 and at least one compound chosen among a pigment, a binder, a latex, a solvent, a detergent compound, a cosmetic compound, an adhesive compound, and combinations thereof.

14. A method for controlling the viscosity of an aqueous formulation, the method comprising addition in the aqueous formulation:
   of at least one composition according to claim 1; or
   of at least one combination of the compounds (a) and (b) defined according to claim 1.

15. The aqueous composition according to claim 1, wherein the non-ionic compound (b) is chosen among non-substituted sucroesters, non-substituted sucroethers, and combinations thereof.

16. The aqueous composition according to claim 1, consisting of:
   at least 40% by weight of the water;
   the at least one polyalkoxylated compound (a); and
   the at least one non-ionic compound (b).

* * * * *